(12) United States Patent
Mitchnick et al.

(10) Patent No.: US 9,274,106 B2
(45) Date of Patent: Mar. 1, 2016

(54) METHODS AND DEVICES FOR DETECTING BINDING EVENTS VIA ZETA-POTENTIAL AND PHARMACOLOGICALLY ACTIVE COMPOUNDS AND DELIVERY SYSTEMS IDENTIFIED THEREBY

(75) Inventors: Mark Mitchnick, East Hampton, NY (US); Andrew Loxley, Philadelphia, PA (US); David Fairhurst, Congers, NY (US); Peter Wagner, Menlo Park, CA (US)

(73) Assignee: Particle Sciences, Inc., Bethlehem, PA (US)

( * ) Notice: Subject to any disclaimer, the term of this patent is extended or adjusted under 35 U.S.C. 154(b) by 543 days.

(21) Appl. No.: 12/593,616

(22) PCT Filed: Apr. 4, 2008

(86) PCT No.: PCT/US2008/059419
§ 371 (c)(1),
(2), (4) Date: Nov. 20, 2009

(87) PCT Pub. No.: WO2009/005868
PCT Pub. Date: Jan. 8, 2009

(65) Prior Publication Data
US 2010/0086608 A1    Apr. 8, 2010

Related U.S. Application Data

(60) Provisional application No. 60/909,974, filed on Apr. 4, 2007, provisional application No. 60/948,740, filed on Jul. 10, 2007.

(51) Int. Cl.
*G01N 33/542* (2006.01)
*G01N 33/543* (2006.01)

(52) U.S. Cl.
CPC ........ *G01N 33/54373* (2013.01); *G01N 33/542* (2013.01); *G01N 33/54313* (2013.01)

(58) Field of Classification Search
CPC .......... G01N 33/542; G01N 33/54313; G01N 33/54373
See application file for complete search history.

(56) References Cited

U.S. PATENT DOCUMENTS

| 6,699,501 | B1 | 3/2004 | Neu et al. ........................ 424/463 |
| 2004/0191837 | A1* | 9/2004 | Harbron et al. ................. 435/7.2 |
| 2004/0203154 | A1 | 10/2004 | Trubetskoy et al. ........... 435/455 |
| 2006/0000722 | A1 | 1/2006 | Parce et al. ................. 205/777.5 |
| 2007/0048797 | A1* | 3/2007 | Su ................................... 435/7.1 |
| 2008/0050842 | A1* | 2/2008 | Golovlev et al. ............. 436/525 |

(Continued)

OTHER PUBLICATIONS

Wikipedia "Ligand" retrieved online on Mar. 6, 2012 (http://en.wikipedia.org/wiki/Ligand) pp. 1-3.*

(Continued)

*Primary Examiner* — Aradhana Sasan
(74) *Attorney, Agent, or Firm* — Licata & Tyrrell P.C.

(57) ABSTRACT

Methods, devices and arrays for measuring a change in zeta-potential of a surface indicative of a binding event are provided. Pharmacologically active compounds and delivery systems for active pharmaceutical ingredients determined to be pharmacologically active or optimized for pharmacological activity or determined to be useful for delivery of the active pharmaceutical ingredient to a target via measurement of a change in zeta-potential of the compound, ingredient or delivery system are also provided.

7 Claims, 2 Drawing Sheets

(56) References Cited

U.S. PATENT DOCUMENTS

2008/0182485 A1* 7/2008 Siddiqui et al. ............ 451/36
2010/0015051 A1* 1/2010 Labhasetwar et al. ....... 424/1.69

OTHER PUBLICATIONS

Goddard et al "Polymer surface modification for the attachment of bioactive compounds"; Prog. Polym. Sci; 32; (May 22, 2007) pp. 698-725.*

Glad et al. "Streaming Potential—A General Affinity Sensor" Biosensors 1986 vol. 2 (2): 89-100.
Koch et al. "Protein Detection with a Novel ISFET-Based Zeta Potential Analyzer" Biosensors & Bioelectronics 1999 vol. 14: 413-421.
Wallin et al. "Enzyme Immunoassay of Benzo[*a*]Pyrene Conjugated to DNA, RNA and Microsomal Proteins Using a Monoclonal Antibody" Cancer Letters 1984 vol. 22 (2): 163-170.

* cited by examiner

METHODS AND DEVICES FOR DETECTING BINDING EVENTS VIA ZETA-POTENTIAL AND PHARMACOLOGICALLY ACTIVE COMPOUNDS AND DELIVERY SYSTEMS IDENTIFIED THEREBY

This patent application is a U.S. National Stage Application of PCT Patent Application No. PCT/US2008/059419, filed Apr. 4, 2008, which claims the benefit of priority from U.S. Provisional Patent Application Ser. No. 60/948,740, filed Jul. 10, 2007 and U.S. Provisional Patent Application Ser. No. 60/909,974, filed Apr. 4, 2007, teachings of each of which are herein incorporated by reference in their entirety.

FIELD OF THE INVENTION

The present invention relates to the use of zeta-potential to detect binding events on surfaces. The present invention also relates to devices for detecting binding events on surfaces comprising a means for measuring zeta-potential. The methods and devices of the present invention are useful in screening for and identifying ligands for a selected surface. Such binding detection may be useful, for example, in identifying drugs or other systems where the binding of one entity to another is important and wherein high throughput screening is of benefit. Pharmacologically active compounds and delivery systems determined to be active or optimized through investigation of binding of the compound or delivery system to a surface via measurement of zeta-potential are also provided.

BACKGROUND OF THE INVENTION

The generation of a streaming potential induced by changes in the zeta-potential has been used to build a general affinity sensor which measures protein interactions (Koch et al. Biosensors & Bioelectronics 1999 14:413-421). The capture agents in this set-up are immobilized on the inside of a capillary in connection with two ISFET sensors on each side of the capillary. The zeta-potential induced streaming potential difference between the two ISFETS is measured. Also see Wallin et al. Cancer Lett. 1984 March; 22(2):163-70 and Glad et al. Biosensors 1986; 2(2): 89-100.

SUMMARY OF THE INVENTION

An aspect of the present invention relates to a method of detecting surface binding events which comprises detecting a change in zeta-potential of a surface in the presence of a potential ligand for the surface itself or a coating on the surface. A change in zeta-potential is indicative of the ligand binding to the surface or surface coating.

Another aspect of the present invention relates to a device for detecting surface binding events, said device comprising a means for detecting change in zeta-potential of a surface or surface coating in the presence of a potential ligand.

Another aspect of the present invention relates to a zeta-potential array for use in high throughput screening of potential ligands for a surface or surface coating.

The methods, devices and arrays of the present invention are useful in identifying ligands for a selected surface or surface coating. Ligands identified via the methods, devices or arrays of the present invention may be useful as, for example, but not limited to, pharmacologically active compounds or delivery systems for active pharmaceutical ingredients, coating materials, coupling agents and reactive materials.

Accordingly, another aspect of the present invention relates to a pharmacologically active compound or active pharmaceutical ingredient determined to be active or optimized to be active through investigation of its binding to a surface via measurement of its zeta-potential.

Yet another aspect of the present invention relates to a delivery system for a pharmacologically active compound or active pharmaceutical ingredient determined to be useful in delivery of the active compound or ingredient to a target or optimized for delivery of the active compound or ingredient to a target through investigation of its binding to a surface via measurement of its zeta-potential.

DETAILED DESCRIPTION OF THE INVENTION

Figure 1:
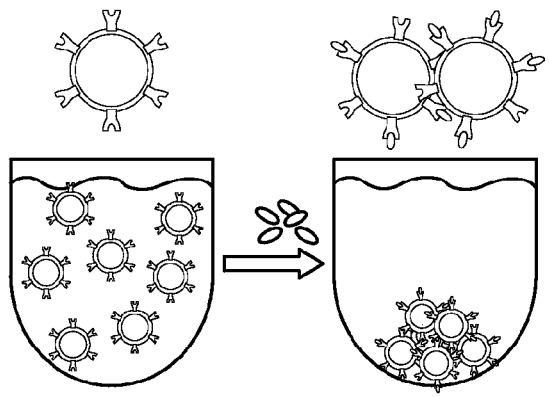
FIG. 1 is a diagram showing the principle of a zeta-potential-based assay of the present invention referred to herein as bead aggregation mode.

It has now been found that changes in the zeta-potential of a surface in the presence of potential ligands are indicative of a binding event.

Zeta-potential is a measure of surface charge on, for example, a microscopic particle. The zeta-potential has a substantial impact on both the stability and aggregation of particles in colloidal suspensions. Streaming potential is essentially the zeta-potential of a macroscopic surface. Accordingly, detection of changes in the zeta-potential is also useful in systems with larger surface than particles.

For purposes of the present invention, by zeta-potential, it is meant any measurement of surface charge independent of the surface size/shape.

The present invention provides methods, devices and arrays for measuring zeta-potential to detect binding events of surfaces in the presence of potential ligands.

By "surface" or "surfaces" as used herein it is meant to include, but is not limited to, particle surfaces, macroscopic surfaces and target coated surfaces to which a ligand can bind.

By "particle", as used herein, it is meant to be inclusive of molecules ranging in diameter from approximately 1-2 nm up to 10-100 microns or more. Exemplary particles for which the zeta-potential can be measured to detect binding events include, but are not limited to, large aggregated proteins, macromolecules and polyelectrolytes, coated beads (inorganic and organic colloids) and whole cells or virus. By particle it is also meant to be inclusive of drugs including, but not limited to, small organic molecules, oligonucleotides, oligopeptides, peptides, proteins carbohydrates, surface active agents and polyelectrolytes.

Examples of macroscopic surfaces include, but are not limited to, macroscopic beads coated with a pharmacological target such as, but not limited to, a receptor or enzyme, where the coated beads are subjected to a variety of potential pharmacologically active compounds or active pharmaceutical ingredients. The binding of a potential ligand such as a potential pharmacologically active compound or pharmaceutically active ingredient to that coated bead would be indicative of a drug/target interaction and is detectable by the change in zeta-potential.

Similarly, a target can be used to coat a surface to produce a target coated surface and the target coated surface, upon exposure to potential ligand such as a pharmacologically active compound or active pharmaceutical ingredient, will change as measured by zeta-potential as a function of the extent and rate of drug/target binding.

By "ligand", as used herein, it is meant any species that has a charge different from the surface under some conditions and that can be adsorbed.

The methods, devices and arrays of the present invention are thus useful, for example, for a given surface such as a particle that has a coating containing a group or functional moiety that is specific to a ligand such as a drug. In this embodiment, any binding/adsorption of the drug to the particle is detected as a change in zeta-potential. For example, a library of small molecules can be screened for changes in zeta-potential in the presence of soluble GP120 (HIV envelope protein) indicative of binding of the small molecule to soluble GP120 and therefore potential utility as a drug. Alternatively, a library of potential drugs can be screened for changes in zeta-potential in the presence of a bead coated with a drug target such as an enzyme indicative of binding of the potential drug to the enzyme.

For the method of the present invention, the zeta-potential of a surface particle is first determined. The surface is then contacted with a potential ligand or ligands and the zeta-potential is re-measured. A change in zeta-potential of the surface in the presence of the potential ligand is indicative of the potential ligand binding to the surface.

In some embodiments of the method of the present invention, the rate of binding is inactive or independent of the degree of attraction or attachment.

In some embodiments of the method of the present invention, a second potential ligand is introduced to compete for the surface or to bind to the first potential ligand itself.

Various detection modes for zeta-potential-based assays in accordance with the present invention can be used. In a preferred embodiment, the detection mode is incorporated into a handheld device or instrument.

For example, if only a threshold yes/no answer is needed with respect to a specific recognition/binding event (e.g. similar to pregnancy tests), a colloidal particle system can established which is close to the aggregation point. Upon binding of ligands by capture agents (immobilized on the colloidal particles), the zeta-potential of the particles is changed, leading to aggregation. Aggregation allows for a very simple visual/optical readout of the assay results. This zeta-potential-based assay of the present invention is referred to as bead aggregation mode. The principle of operation of this zeta-potential-based assay is depicted in the diagram of FIG. 1.

Figure 2:
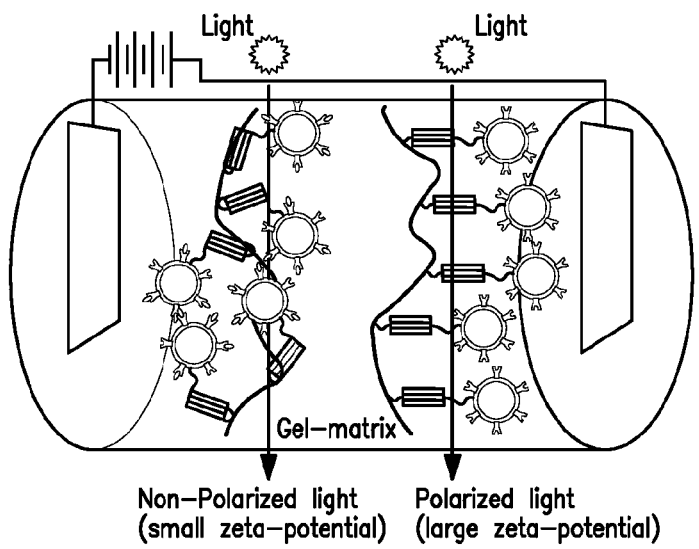
FIG. 2 is a diagram of another exemplary embodiment of a zeta-potential-based assay of the present invention wherein liquid crystal/particles are attached to a gel via polarization-active linker molecules.

In an alternative embodiment, the zeta-potential of capture particles is read optically by attaching the capture particles via crosslinker molecules to, for example, the matrix of a very porous gel. The crosslinker molecules have incorporated some rigid, polarization-active molecules. Upon change in the zeta-potential of the capture particles (e.g. by binding of analyte), the capture particles will be more or less oriented in the applied electric field, which leads to a change in the polarization degree of incoming light. The principle of operation of this exemplary embodiment of zeta-potential-based assay of the present invention, wherein liquid crystal/particles are attached to a gel via polarization-active linker molecules, is depicted in FIG. 2.

Figure 3:
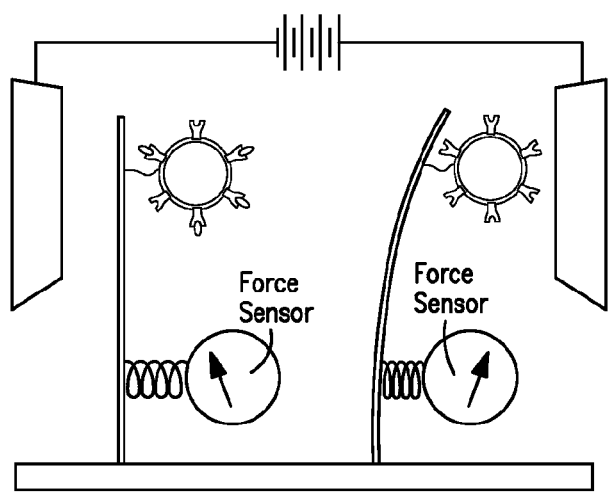
FIG. 3 is a diagram of another exemplary embodiment of a zeta-potential-based assay of the present invention wherein a ζ-potential force sensor is used to determine the zeta-potential induced attraction of coated particles towards one of the electrodes.

In another exemplary embodiment, a MEMS integrated force sensor such as a micro-cantilever with attached particles can be used to determine the zeta-potential-induced attraction of the coated particles towards one of the electrodes. The principle of operation of this exemplary embodiment of zeta-potential-based assay of the present invention is depicted in the ζ-potential force sensor shown in FIG. 3.

Figure 4:
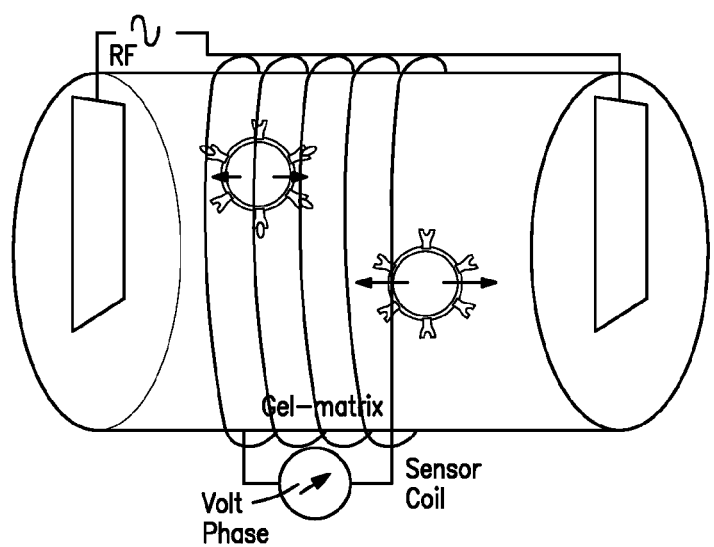
FIG. 4 is a diagram of yet another exemplary embodiment of a zeta-potential-based assay of the present invention comprising an electro-magnetic detection system.

In yet another exemplary embodiment of a zeta-potential-based assay of the present invention, an electric field is used to induce movement of magnetic capture-particles based on their zeta-potential. With high-frequency (RF) voltage applied, the particle mobility will induce a change in the induced voltage (e.g. phase shift) in a magnetic sensor coil wrapped around the sample volume. The principle of operation of this exemplary embodiment of the present invention is depicted in the electro-magnetic detection system of FIG. 4. This embodiment of the present invention eliminates the need for costly laser optic-based detection systems and makes the reader very inexpensive.

Additional means for measuring changes in zeta-potential in accordance with the present invention include, but are in no way limited to, IEF (isoelectric focusing) of capture particles, measurement of assay-specific time-delay of a dye-coated bead to reach a specific position in a long tube by light absorption (elimination of laser diode) and surface-based assays such as competition assays.

In addition to detecting binding of a potential ligand to a surface, changes in zeta-potential measured in accordance with the methods and devices of the present invention can be used to determine the rate of binding as an indication of affinity. Additionally, once a first ligand, referred to as ligand A is bound, another ligand, referred to as ligand B, can be introduced and relative binding strengths can be determined as ligand A is displaced (or not) by ligand B. In one embodiment, this is done by determining the zeta-potential for ligand A and then for ligand B separately. This allows the determination of the optimum concentration: that which provides the maximum positive or negative zeta-potential. Then surface plus ligand A can be challenged by ligand B and the difference in zeta-potential can be quantified.

The present invention also provides zeta-potential arrays comprising a number of zeta-potential cells in parallel for high throughput screening.

The methods, devices and arrays of the present invention are thus useful in identifying ligands for any selected surface or surface coating. Ligands identified via the methods, devices or arrays of the present invention may be useful as, for example, but not limited to, pharmacologically active compounds or delivery systems for active pharmaceutical ingredients, coating materials, coupling agents and reactive materials.

The present invention thus also relates to pharmacologically active compounds or active pharmaceutical ingredients determined to be pharmacologically active or optimized for pharmacological activity via measurement of zeta-potential of a compound or ingredient in a binding assay of the compound or ingredient to a target coated surface, preferably a therapeutic target coated surface. Pharmacologically active compounds of the present invention can be identified or optimized via measurement of zeta-potential in binding assays conducted throughout a range of physiologic pHs and/or salt concentrations. Pharmacologically active compounds of the present invention can also be identified or optimized via measurement of zeta-potential in binding assays conducted using target coated surfaces that are in a physiologic relevant state such as coated with endogenous biomolecules or in confirmations reflective of their natural state. In addition, pharmacologically active compounds of the present invention can be identified or optimized via measurement of zeta-potential in binding assays conducted using target coated surfaces that are not coated with materials such as buffers that would alter the surface properties of the target.

Pharmacologically active compounds and active pharmaceutical ingredients identified in the accordance with the present invention include, but are not limited to, small molecules, peptides, proteins, sugars, glycoproteins, DNA based molecules or RNA based molecules.

The present invention also relates to delivery systems for an active pharmaceutical ingredient determined to be useful in delivering an active pharmaceutical ingredient to a target or optimized for delivery of an active pharmaceutical ingredient to a target via measurement of zeta-potential of the delivery system in a binding assay of the delivery system to a target coated surface, preferably a therapeutic target coated surface. Delivery systems identified in accordance with the present invention include, but are not limited to, particles, molecules, polymers and devices. Particles useful as delivery systems of the present invention preferably range in size from 5 nm to 100 microns, more preferably 20 nm to 1000 nm, more preferably 50 nm to 500 nm.

While the methods described herein are useful in identifying pharmacologically active compounds and active pharmaceutical ingredients and delivery systems for essentially any therapeutic target, measurement of zeta-potential is particularly useful in selection and/or design of antimicrobial compounds. In this embodiment, compounds, ingredients and/or delivery systems can be identified which bind to a microbial particle as a whole based upon measurement of zeta-potential. Further, compounds ingredients and/or delivery systems can be compared for their efficacy by titrating the actual amount of compound ingredient and/or delivery system required to neutralize the surface charge of a microbe which is determined by monitoring changes in zeta-potential. Zeta-potential of the microbe can be measured over a range of conditions relevant for the microbial infection. For example, the zeta-potential of a sexually transmitted microbe can be measured within a range of conditions typical of the vaginal environment pre- and post-intercourse. Exemplary environmental parameters that can be varied to model conditions relevant for microbial infections include, but are not limited to, pH, solution conductivity, ionic strength, electrolyte concentrations, temperature and solution viscosity. A preferred method for measuring the zeta-potential of microbes and identifying compounds, ingredients and delivery systems of the present invention is microelectrophoresis.

What is claimed is:

1. A method of detecting binding of a ligand consisting of:
   (a) measuring zeta-potential of a surface, wherein the surface is a particle in a physiologic relevant state having coated on the surface a moiety being either a drug or biomolecule for which a drug is a target;
   (b) contacting the surface with a potential ligand for the moiety on the surface; and
   (c) measuring zeta-potential of the surface in the presence of the potential ligand wherein a change in zeta-potential of the surface in the presence of the potential ligand is indicative of the potential ligand being a ligand for the moiety and binding to the moiety.

2. The method of claim 1 wherein rate of potential ligand binding is indicative of degree of attraction or attachment.

3. The method of claim 1 where a second potential ligand is introduced to compete for the moiety on the surface or to bind to the first potential ligand.

4. The method of claim 1 wherein the measurement of changes in zeta-potential is conducted throughout a range of physiologic pHs and salt concentrations.

5. The method of claim 1 wherein the surface in the physiologic relevant state is coated with endogenous biomolecules or is in a conformation reflective of its natural state.

6. The method of claim 1 wherein the surface is a microbe.

7. The method of claim 1 wherein the particle is selected from the group consisting of a large aggregated protein, a macromolecule, a polyelectrolyte, a coated bead, a whole cell or virus, and a drug.

\* \* \* \* \*